United States Patent
Zhao et al.

(10) Patent No.: US 12,029,760 B2
(45) Date of Patent: Jul. 9, 2024

(54) COMPOSITIONS AND METHODS FOR GENE EDITING IN T CELLS USING CRISPR/Cpf1

(71) Applicant: THE TRUSTEES OF THE UNIVERSITY OF PENNSYLVANIA, Philadelphia, PA (US)

(72) Inventors: Yangbing Zhao, Lumberton, NJ (US); Jiangtao Ren, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1104 days.

(21) Appl. No.: 16/609,628

(22) PCT Filed: May 2, 2018

(86) PCT No.: PCT/US2018/030644
§ 371 (c)(1),
(2) Date: Oct. 30, 2019

(87) PCT Pub. No.: WO2018/204493
PCT Pub. Date: Nov. 8, 2018

(65) Prior Publication Data
US 2020/0054679 A1 Feb. 20, 2020

Related U.S. Application Data

(60) Provisional application No. 62/501,371, filed on May 4, 2017.

(51) Int. Cl.
| | | |
|---|---|---|
| A61K 35/17 | (2015.01) | |
| C12N 9/22 | (2006.01) | |
| C12N 15/10 | (2006.01) | |
| C12N 15/117 | (2010.01) | |
| C12N 15/90 | (2006.01) | |
| A61K 39/00 | (2006.01) | |
| A61P 35/00 | (2006.01) | |
| A61P 37/02 | (2006.01) | |

(52) U.S. Cl.
CPC ............. *A61K 35/17* (2013.01); *C12N 9/22* (2013.01); *C12N 15/102* (2013.01); *C12N 15/117* (2013.01); *C12N 15/90* (2013.01); *A61K 2039/5158* (2013.01); *A61P 35/00* (2018.01); *A61P 37/02* (2018.01); *C12N 2310/122* (2013.01); *C12N 2310/20* (2017.05); *C12N 2310/315* (2013.01)

(58) Field of Classification Search
None
See application file for complete search history.

(56) References Cited

U.S. PATENT DOCUMENTS

| 9,790,490 B2 * | 10/2017 | Zhang | ............. C12N 15/10 |
|---|---|---|---|
| 2017/0067021 A1 * | 3/2017 | Moriarity | .......... C12N 9/22 |

FOREIGN PATENT DOCUMENTS

| WO | 2016073955 A2 | 5/2016 |
|---|---|---|
| WO | 2017064546 A1 | 4/2017 |

OTHER PUBLICATIONS

Lurquin, "Gene Transfer by Electroporation" 7 Molecular Biotechnology 5-35 (Year: 1997).*
Extended European Search Report issued in App. No. EP18795128.0, dated Dec. 17, 2020, 12 pages.
International Search Report and Written Opinion issued in App. No. PCT/US18/30644, dated Sep. 19, 2018, 15 pages.
Zetsche, B. et al., "Cpf1 is a single RNA-guided endonuclease of a Class 2 CRISPR-Cas system," Cell, vol. 163, No. 3, pp. 759-771 (2015).

* cited by examiner

*Primary Examiner* — Nancy J Leith
(74) *Attorney, Agent, or Firm* — Saul Ewing LLP; Kathryn Doyle

(57) ABSTRACT

The present invention includes compositions and methods for modifying primary T cells. In one aspect, the invention comprises administering to a cell a stem-loop Clustered Regularly Interspaced Short Palindromic Repeats (CRISPR) RNA (st-crRNA) and a Cpf1 enzyme.

12 Claims, 10 Drawing Sheets

Specification includes a Sequence Listing.

SEQUENCE LISTING

```
<160> NUMBER OF SEQ ID NOS: 9

<210> SEQ ID NO 1
<211> LENGTH: 20
<212> TYPE: RNA
<213> ORGANISM: Artificial Sequence
<220> FEATURE:
<223> OTHER INFORMATION: sgRNA TRAC: synthesized sequence

<400> SEQUENCE: 1
agagucucuc agcugguaca                                               20

<210> SEQ ID NO 2
<211> LENGTH: 20
<212> TYPE: RNA
<213> ORGANISM: Artificial Sequence
<220> FEATURE:
<223> OTHER INFORMATION: sgRNA TRBC: synthesized sequence
```

```
<400> SEQUENCE: 2
ugggagaucu cugcuucuga                                           20

<210> SEQ ID NO 3
<211> LENGTH: 20
<212> TYPE: RNA
<213> ORGANISM: Artificial Sequence
<220> FEATURE:
<223> OTHER INFORMATION: sgRNA B2m: synthesized sequence

<400> SEQUENCE: 3
cgcgagcaca gcuaaggcca                                           20

<210> SEQ ID NO 4
<211> LENGTH: 23
<212> TYPE: RNA
<213> ORGANISM: Artificial Sequence
<220> FEATURE:
<223> OTHER INFORMATION: crRNA TRAC: synthesized sequence

<400> SEQUENCE: 4
gagucucuca gcugguacac ggc                                       23

<210> SEQ ID NO 5
<211> LENGTH: 23
<212> TYPE: RNA
<213> ORGANISM: Artificial Sequence
<220> FEATURE:
<223> OTHER INFORMATION: crRNA TRBC: synthesized sequence

<400> SEQUENCE: 5
agccaucaga agcagagauc ucc                                       23

<210> SEQ ID NO 6
<211> LENGTH: 23
<212> TYPE: RNA
<213> ORGANISM: Artificial Sequence
<220> FEATURE:
<223> OTHER INFORMATION: crRNA B2m: synthesized sequence

<400> SEQUENCE: 6
auccauccga cauugaaguu gac                                       23

<210> SEQ ID NO 7
<211> LENGTH: 42
<212> TYPE: RNA
<213> ORGANISM: Artificial Sequence
<220> FEATURE:
<223> OTHER INFORMATION: crRNA: synthesized sequence

<400> SEQUENCE: 7
aauuucuacu cuuguagaua gccaucagaa gcagagaucu cc                  42

<210> SEQ ID NO 8
<211> LENGTH: 101
<212> TYPE: DNA
<213> ORGANISM: Artificial Sequence
<220> FEATURE:
<223> OTHER INFORMATION: sgRNA: synthesized sequence
<220> FEATURE:
<221> NAME/KEY: MISC_FEATURE
<222> LOCATION: (1)..(101)
<223> OTHER INFORMATION: DNA/RNA molecule
```

```
<400> SEQUENCE: 8
gtcacctcca atgactaggg guuuuagagc uagaaauagc aaguuaaaau aaggcuaguc      60
cgccaucaac uugaaaaagu ggcaccgagu cggugcuuuu u                         101

<210> SEQ ID NO 9
<211> LENGTH: 58
<212> TYPE: DNA
<213> ORGANISM: Artificial Sequence
<220> FEATURE:
<223> OTHER INFORMATION: PMS-crRNA: synthesized sequence
<220> FEATURE:
<221> NAME/KEY: MISC_FEATURE
<222> LOCATION: (1)..(58)
<223> OTHER INFORMATION: DNA/RNA molecule

<400> SEQUENCE: 9
gggugaaaaa guucataauu ucuacucuug uagauagcca ucagaagcag agaucucc        58
```

COMPOSITIONS AND METHODS FOR GENE EDITING IN T CELLS USING CRISPR/Cpf1

CROSS-REFERENCE TO RELATED APPLICATION

The present application is a 35 U.S.C. § 371 national phase application from, and claims priority to, International Patent Application No. PCT/US2018/030644, filed on May 2, 2018, which is entitled to priority under 35 U.S.C. § 119(e) to U.S. Provisional Patent Application No. 62/501,371 filed on May 4, 2017, each of which applications-is hereby incorporated by reference in their entirety herein.

REFERENCE TO AN ELECTRONIC SEQUENCE LISTING

The Sequence Listing submitted herewith as an ASCII txt file named "046483-7163US1," created on May 12, 2023 and having a size of 2,334 bytes, is herein incorporated by reference in its entirety.

STATEMENT REGARDING FEDERALLY SPONSORED RESEARCH OR DEVELOPMENT

This invention was made with government support under 2R01CA120409 awarded by the National Institutes of Health. The government has certain rights in the invention.

BACKGROUND OF THE INVENTION

Early chimeric antigen receptor (CAR) T cell clinical data treating cancers has shown promising results, but progress in CAR immunotherapy for cancer and infectious diseases is hampered by the lack of readily available, potent, antigen and patient-specific T lymphocytes. Highly personalized CAR T cell immunotherapy treatment of patients can be rather expensive and time consuming. Autologous T cells from patients with advanced disease may have compromised function and be tolerant to desired antigens, forcing modification of allogeneic donor-derived T cells. And, the endogenous αβ T-cell receptor on infused allogeneic T cells may recognize major and minor histocompatibility antigens in the recipient, leading to graft-versus-host-disease (GVHD). As a result, the majority of current clinical trials infused with autologous CAR T cells rely on immune tolerance to prevent TCR-mediated deleterious recognition of normal tissues after adoptive transfer. This approach has achieved early clinical successes, but is limited by the time and expense required to manufacture patient-specific T cell products. Therefore, a need exists for safer methods of modifying T cells, while minimizing the time and expense to manufacture patient specific T cell products.

Although some reports have claimed to have successfully generated universal T cells that avoid GVHD by disrupting TCR expression, allogeneic T cells can still be rejected by the host's immune system through recognition of the HLA-A molecule. Because of the complicated targeting strategy to manipulate multiple genes, and low efficiency of ZFN and TALEN in T cells, no research to date has achieved the aim of preventing GVHD and host-versus-graft reactions simultaneously. Full depletion of TCR α,β chains and beta-2 microglobin has to be achieved in order to generate truly universal CART cells.

T-cell genome engineering holds great promise for cell-based therapies for cancer, HIV, primary immune deficiencies, and autoimmune diseases, but genetic manipulation of human T cells has been challenging. CRISPR/Cas9 technology is facilitating genome engineering in many cell types including T cells, but the gene editing capability of CRISPR/Cpf1 in human T cells is still illusive.

A need exists for novel compositions and methods for therapeutic genome engineering in primary human T cells. The present invention satisfies this need.

SUMMARY OF THE INVENTION

As described herein, the present invention relates to compositions and methods for gene editing.

One aspect of the invention includes a method of gene editing comprising administering to a cell an exogenous nucleic acid comprising a stem-loop Clustered Regularly Interspaced Short Palindromic Repeats (CRISPR) RNA (st-crRNA) and an exogenous nucleic acid encoding a Cpf1 enzyme.

Another aspect of the invention includes a method of generating a modified T cell by gene editing. The method comprises administering to a T cell an exogenous nucleic acid comprising a st-crRNA and an exogenous nucleic acid encoding a Cpf1 enzyme.

Yet another aspect of the invention includes a genetically modified cell comprising an exogenous nucleic acid encoding a st-crRNA and an exogenous nucleic acid encoding a Cpf1 enzyme.

Still another aspect of the invention includes a method of adoptive cell transfer therapy. The method comprises administering to a subject in need thereof a population of modified cells comprising the modified cell of the present invention.

In another aspect, the invention includes a method of treating a disease or condition in a subject. The method comprises administering to a subject in need thereof a population of modified cells comprising the modified cell of the present invention.

In various embodiments of the above aspects or any other aspect of the invention delineated herein, the cell is a T cell. In one embodiment, the T cell is a primary T cell.

In one embodiment, the administering comprises electroporating the exogenous nucleic acid into the cell. In one embodiment, the electroporating is performed multiple times.

In one embodiment, the Cpf1 enzyme comprises Acidaminococcus Cpf1 (AsCpf1). In one embodiment, the Cpf1 enzyme comprises Lachnospiraceae Cpf1 (LbCpf1).

In one embodiment, the st-crRNA comprises a stem-loop structure on the 3' end of the crRNA. In one embodiment, the st-crRNA comprises a stem-loop structure on the 5' end of the crRNA. In one embodiment, the stem-loop structure further comprises three glycine residues added to the 5' end of the stem loop. In one embodiment, the protospacer region of the st-crRNA further comprises a partial phosphorothioation (PMS) modification.

In one embodiment, the gene editing comprises mutating a gene selected from the group consisting of: TCR α chain constant region (TRAC), TCR β constant region (TRBC), and β-2 microglobulin (B2m).

In one embodiment, the disease or condition is selected from the group consisting of an infectious disease, an autoimmune disease, and a cancer. In one embodiment, the method of the present invention further comprises administering a secondary treatment for the disease or condition.

In one embodiment, the subject is a human.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 1A illustrates the structures of crRNA (SEQ ID NO: 7), sgRNA (SEQ ID NO: 8) and the schematic designs of stem loops and chemical modification sites. Gray letters: stem loop; Star: modification. FIG. 1B depicts gene-targeting efficiency of crRNA with different stem loops. No: no crRNA; Un: unmodified crRNA; Lst: left stem-loop; Mst: middle stem-loop; Rst: right stem-loop. TRAC and TRBC disruption was determined by measuring CD3 expression on T cells via flow cytometry. B2m disruption was determined by measuring B2m or HLA-I expression on T cells via flow cytometry. FIG. 1C is an illustration of chemically modified PMS-crRNA. MS-crRNA: 2'-O-methyl 3'phosphorothioated crRNA; PMS-crRNA: phosphorothioated MS-crRNA (SEQ ID NO:9). FIG. 1D shows gene-targeting efficiency of single-electroporated chemically modified crRNAs. FPMS-crRNA: fully phosphorothioated PMS-crRNA. FIG. 1E shows gene-targeting efficiency of multiple-electroporated chemically modified crRNAs.

FIG. 2A shows guides favoring different RGENs. Three genes, TRAC, TRBC, and B2m, were edited in primary T cells using Cpf1 and wild-type and high-fidelity Cas9-eSpCas9. Ten different guide RNAs were tested for each gene. Gene disruption was measured on the basis of protein expression via flow cytometry. FIG. 2B shows the guide length requirements of different RGENs. TRAC, TRBC and B2m were targeted by different RGENs with truncated guide RNAs. Gene disruption was measured on the basis of protein expression using flow cytometry.

FIG. 3C shows reduced off-target potential of Cpf1 as confirmed by gene targeting with mutated guide RNA. Single base pair mutated guide RNAs were used to test the non-specific guiding of Cpf1 or Cas9. While single mutation within 10 base pairs adjacent to PAM sites reduced targeting efficiency of Cas9, single mutation proximal to PAM sites did not significantly affect the gene targeting efficiency. A single base pair mutation of the guide RNA greatly abolished the gene disruption capability of Cpf1, indicating more specific target recognition of Cpf1 than Cas9.

FIG. 4A shows comparison of gene disruption efficiency of Cas9, AsCpf1 and LbCpf1 in primary T cells with a multiple electroporation protocol. FIG. 4B shows enhanced gene ablation of Cpf1 with stem-loop crRNA. Nearly 2-fold gene disruption was observed using the stem-loop crRNA compared to wild type crRNA in a multiple electroporation protocol.

DETAILED DESCRIPTION

Definitions

Figure 1A:
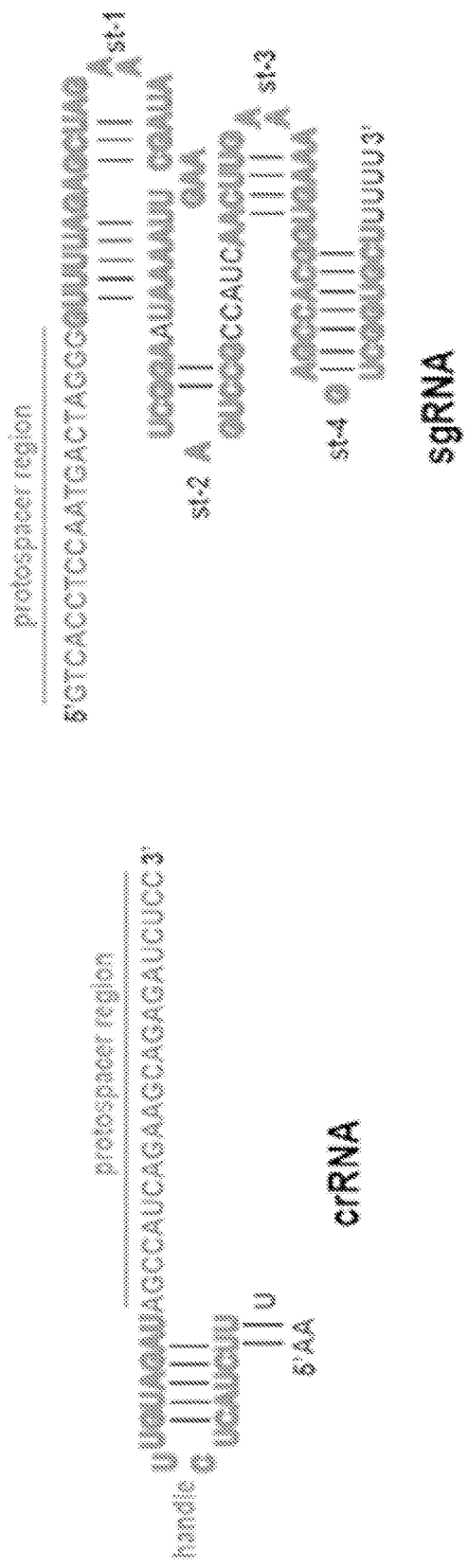
FIGS. 1A-1E are a series of plots and images illustrating that chemical modification and stem-loop structure of crRNA enables efficient gene targeting with Cpf1.
Figure 1A:
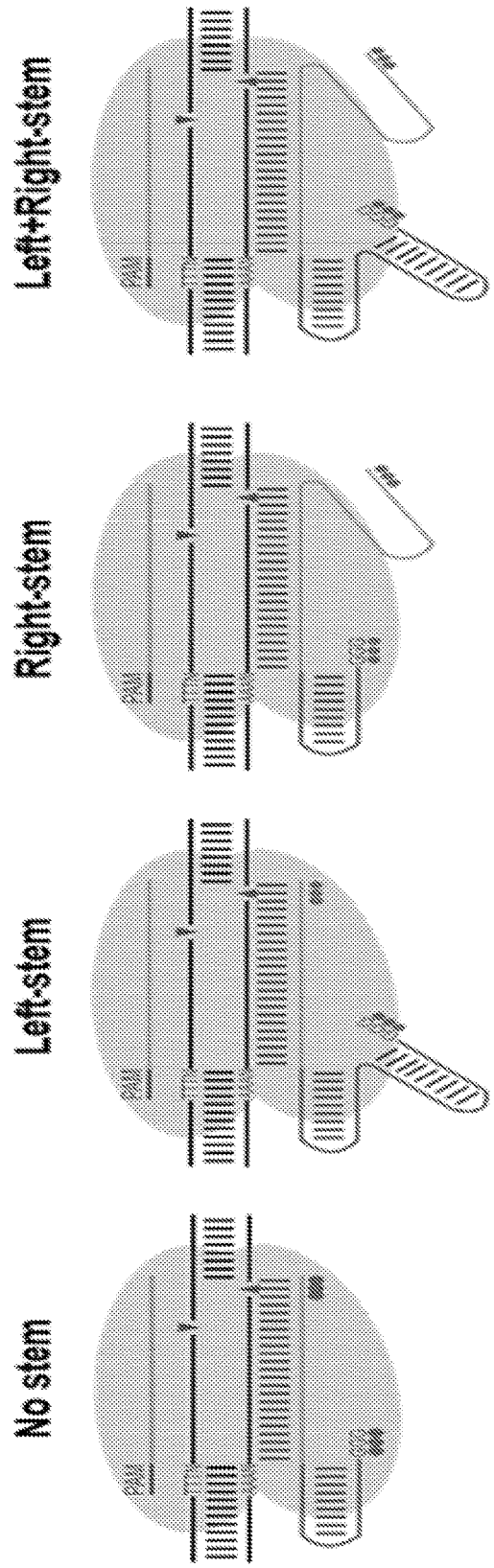

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Allogeneic" refers to any material derived from a different animal of the same species.

"Xenogeneic" refers to any material derived from an animal of a different species.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs has specificity to a selected target, for example a B cell surface receptor. CARs may also comprise an intracellular activation domain, a transmembrane domain and an extracellular domain comprising a tumor associated antigen binding region. In some aspects, CARs comprise an extracellular domain comprising an anti-B cell binding domain fused to CD3-zeta transmembrane and intracellular domain The term "cleavage" refers to the breakage of covalent bonds, such as in the backbone of a nucleic acid molecule or the hydrolysis of peptide bonds. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

The term "immune response" as used herein is defined as a cellular response to an antigen that occurs when lymphocytes identify antigenic molecules as foreign and induce the formation of antibodies and/or activate lymphocytes to remove the antigen.

When "an immunologically effective amount," "an autoimmune disease-inhibiting effective amount," or "therapeutic amount" is indicated, the precise amount of the compositions of the present invention to be administered can be determined by a physician or researcher with consideration of individual differences in age, weight, tumor size, extent of infection or metastasis, and condition of the patient (subject).

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compositions and methods for making and using genetically modified cells. The genetically modified cells comprise an exogenous nucleic acid encoding a stem-loop Clustered Regularly Interspaced Short Palindromic Repeats (CRISPR) RNA (st-crRNA) and an exogenous nucleic acid encoding a Cpf1 enzyme. Certain aspects of the invention include methods of gene editing in a cell and methods of generating modified cells. Also included are methods and pharmaceutical compositions comprising the modified cells for adoptive therapy and treating a disease or condition.

The data disclosed herein demonstrate efficient genome engineering in human T cells using Cpf1 and crRNA. CRISPR/Cpf1 gene editing ablated the TCR alpha chain, an essential component of the TCR/CD3 complex. Cpf1 gene editing caused up to 80% of cells to lose high-level cell-surface expression of the TCR. These results establish CRISPR/Cpf1 for use in diverse experimental and therapeutic genome engineering applications in primary human T cells.

CRISPR/Cpf1

Clustered regularly interspaced short palindromic repeats (CRISPR) and CRISPR-associated (Cas) proteins, which provide bacteria with adaptive immunity to foreign nucleic acids, have been repurposed for use in targeted genome editing in human cells and other types of cells, as well as in animals and plants. The CRISPR/Cas9 technology originates from type II CRISPR/Cas systems. which consist of one DNA endonuclease protein, Cas9, and two small RNAs, CRISPR RNA (crRNA) and trans-activating crRNA (tracrRNA). The small RNAs or a chimeric single guide RNA (sgRNA) bind Cas9, thus forming an RNA-guided DNA endonuclease (RGEN) complex, and cleave a specific DNA target. Chromosomal double-strand blunt-end breaks (DSBs) are then repaired via homologous recombination (HR) or non-homologous end-joining (NHEJ) and produce genetic modifications.

Cpf1 is another type of RGEN derived from the type V CRISPR system. Cpf1 differs from Cas9 in several ways. First, the function of Cpf1 requires only a crRNA, rather than a crRNA/tracrRNA pair. Second, Cas9 cleavage results in blunt DSBs, whereas Cpf1 cleavage produces cohesive ends. Third, Cpf1 recognizes thymidine-rich DNA sequences, such as the protospacer adjacent motifs (PAMs) at the 5' ends of target sequences (e.g., 5'-TTTN-3'). These features of Cpf1 broaden the range of CRISPR-endonuclease-editable genomic sites beyond the guanosine-rich sequences recognized by various Cas9 enzymes. Cpf1 requires only crRNA and does not utilize tracrRNA, and the Cpf1 crRNAs are significantly shorter than the ~100-nucleotide sgRNAs required by Cas9, thereby offering cheaper and simpler guide RNA production. This property is particularly useful when chemically modified guides are used. Chemically modified sgRNA has recently been shown to enhance the gene-targeting efficiency in human primary cells; however, until the present study the extent to which chemically modified crRNA can aid in gene targeting by Cpf1 had yet to be investigated.

Researchers have reported better gene-targeting specificity of Cpf1 than Cas9 in certain cell types, on the basis of whole-genome off-target analysis. The specificity of Cpf1 in T cells is not understood.

T cell-targeted genome editing holds great potential to facilitate T cell-based cancer immunotherapy. Gene editing in primary T cells with Cas9-sgRNA has been extensively studied. However, the gene-editing potential of Cpf1 in T cells remains to be explored. In the present study. the effect of structural and chemical modifications on crRNAs and the efficiency and specificity of gene editing using Cpf1-crRNA in T cells were examined.

Compositions

Certain aspects of the invention include genetically modified cells. In one aspect, the invention includes a genetically modified cell comprising an exogenous nucleic acid encoding a st-crRNA and an exogenous nucleic acid encoding a Cpf1 enzyme. The genetically modified cell can be any type of cell including but not limited to T lymphocytes, B lymphocytes, NK cells, monocytes, macrophages, neutrophils, epithelial cells, hematopoietic stem cells, and Induced Pluripotent Stem Cells (iPS).

In one embodiment, the genetically modified cell is a human cell. In another embodiment, the cell genetically modified cell is an autologous cell.

In certain embodiments, the genetically modified cell is a T cell. The T cell can be any type of T cell known in the art including but not limited to CD3+ cells, CD4+ cells, CD8+ cells, T regulatory cell (Treg), T helper cells (Th1 and T2), cytotoxic T cells (CTLs), Natural killer T cells (NKT cells), gamma delta T cells, effector T cells, memory T cells, and naïve T cells. In one embodiment, the genetically modified T cell is a primary T cell. In another embodiment, the cell genetically modified cell is an autologous T cell.

The genetically modified cells of the invention comprise an exogenous nucleic acid encoding a Cpf1 enzyme. The Cpf1 enzyme can be derived from any genera of microbes including but not limited to Parcubacteria, Lachnospiraceae, *Butyrivibrio, Peregrinibacteria, Acidaminococcus, Porphyromonas*, Lachnospiraceae, Porphromonas, *Prevotella*, Moraxela, Smithella, Leptospira, Lachnospiraceae, *Francisella*, Candidatus, and *Eubacterium*. In one embodiment, Cpf1 is derived from a species from the Acidaminococcus genus (AsCpf1). In another embodiment, Cpf1 is derived from a species from the Lachnospiraceae genus (LbCpf1).

The genetically modified cells of the present invention comprise an exogenous nucleic acid encoding a CRISPR RNA with at least one additional stem-loop structure attached to it (st-crRNA). Native crRNAs are generally comprised of about 42-44 nucleotides (a 19 nucleotide long repeat sequence and a 23-15 nucleotide spacer sequence) and a single stem loop structure, also known as the 'handle' structure. crRNAs of the present invention include at least one additional stem loop structure (in addition to the handle) and are herein referred to as stem-loop crRNAs (st-crRNAs). The additional step loop structure(s) can be attached to the 5' end of the crRNA and/or to the 3' end of the crRNA. The st-RNAs can comprise one additional stem loop structure or more than one additional stem loop structure. In one embodiment, the st-crRNA comprises a stem-loop structure on the 5' end of the crRNA adjacent to the handle. In another embodiment, the st-crRNA comprises a stem-loop structure on the 3' end of the crRNA. The st-RNAs can further comprise a modification. In one embodiment, the st-RNA further comprises three glycine residues added to the 5' end of the stem loop. In another embodiment, the protospacer region of the st-crRNA further comprises a partial phosphorothioation (PMS) modification. In yet another embodiment, the st-RNA further comprises three glycine residues added to the 5' end of the stem loop and a partial phosphorothioation (PMS) modification in the protospacer region.

The st-crRNAs of the present invention can be designed to target any gene of interest. For example, in certain embodiments, the crRNAs are designed to target the TCR α chain constant region (TRAC) and/or the TCR β constant region (TRBC), and/or the β-2 microglobulin (B2m) gene.

Methods

In one aspect, the invention includes a method of gene editing. The method comprises administering to a cell an exogenous nucleic acid comprising a stem-loop Clustered Regularly Interspaced Short Palindromic Repeats (CRISPR) RNA (st-crRNA) and an exogenous nucleic acid comprising a Cpf1 enzyme. In one embodiment, the cell to be edited is a T cell. In another embodiment, the cell is a primary T cell.

Another aspect of the invention includes a method of generating a modified T cell. The method comprises administering to a cell an exogenous nucleic acid comprising a st-crRNA and an exogenous nucleic acid comprising a Cpf1 enzyme.

In certain embodiments of the invention, the exogenous nucleic acids are administering by electroporating them into the cell. In certain embodiments, the cell is electroporated multiple times. For example, the cell may be electroporated a first time with a first st-crRNA, then electroporated a second time with a second st-crRNA.

The Cpf1 enzyme can be derived from any genera of microbes including but not limited to Parcubacteria, Lachnospiraceae, *Butyrivibrio*, Peregrinibacteria, Acidaminococcus, *Porphyromonas*, Lachnospiraceae, Porphromonas, *Prevotella*, Moraxela, Smithella, Leptospira, Lachnospiraceae, *Francisella*, Candidatus, and *Eubacterium*. In one embodiment, Cpf1 is derived from Acidaminococcus (AsCpf1). In another embodiment, Cpf1 is derived from Lachnospiraceae (LbCpf1).

Certain aspects of the invention include a CRISPR-RNA (crRNA) with a stem-loop attached to it (st-crCRNA). The stem-loop structure can be attached to the 3' end of the crRNA and/or the 5'end of the crRNA. The stem loop can further comprise an additional three glycine residues added to the 5' end of the stem loop. The protospacer region of the st-crRNA can further comprises a partial phosphorothioation (PMS) modification. In one embodiment, the st-RNA further comprises three glycine residues added to the 5' end of the stem loop and a partial phosphorothioation (PMS) modification in the protospacer region.

The gene editing methods of the present invention can be used to mutate any gene of interest. For example the method can mutate the TCR a chain constant region (TRAC) and/or the TCR β constant region (TRBC) and/or the β-2 microglobulin (B2m). The methods can be used in conjunction with other CRISPR systems, for example with Type I or Type II CRISPR systems. In one non-limiting example, the Cpf1/st-crRNA gene editing system can be used in conjunction with the CRISPR/Cas 9 system. Use of the two systems in a multiplex fashion would allow broader screening and target selectivity.

Introduction of Nucleic Acids

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Moreover, the nucleic acids may be introduced by any means, such as transducing the cells, transfecting the cells, and electroporating cells. One nucleic acid may be introduced by one method and another nucleic acid may be introduced into the cell by a different method.

RNA

In one embodiment, the nucleic acids introduced into the cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric membrane protein. By way of example, the template encodes an antibody, a fragment of an antibody or a portion of an antibody. By way of another example, the template comprises an extracellular domain comprising a single chain variable domain of an antibody, such as anti-CD3, and an intracellular domain of a co-stimulatory molecule. In one embodiment, the template for the RNA chimeric membrane protein encodes a chimeric membrane protein comprising an extracellular domain comprising an antigen binding domain derived from an antibody to a co-stimulatory molecule, and an intracellular domain derived from a portion of an intracellular domain of CD28 and 4-1BB.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5', to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenbom and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA is electroporated into the cells, such as in vitro transcribed RNA.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Therapy

The modified cells described herein may be included in a composition for therapy. The composition may include a pharmaceutical composition and further include a pharmaceutically acceptable carrier. A therapeutically effective amount of the pharmaceutical composition comprising the modified cells may be administered.

In one aspect, the invention includes a method for adoptive cell transfer therapy comprising administering to a subject in need thereof a modified cell of the present invention. In another aspect, the invention includes a method of treating a disease or condition in a subject comprising administering to a subject in need thereof a population of modified cells.

In certain embodiments, the modified cells are T cells. The T cells can be primary T cells. The modified T cells generated as described herein possess T cell function.

The modified cells can be administered to a mammal, preferably a human, to suppress an immune reaction, such as those common to autoimmune diseases such as diabetes, psoriasis, rheumatoid arthritis, multiple sclerosis, GVHD, enhancing allograft tolerance induction, transplant rejection, and the like. In addition, the cells of the present invention can be used for the treatment of any condition in which a diminished or otherwise inhibited immune response, especially a cell-mediated immune response, is desirable to treat or alleviate the disease. In one aspect, the invention includes treating a condition, such as an autoimmune disease, in a subject, comprising administering to the subject a therapeutically effective amount of a pharmaceutical composition comprising a population of modified cells. Examples of autoimmune disease include but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

The modified cells generated as described herein can also be expanded and used to treat inflammatory disorders. Examples of inflammatory disorders include but are not limited to, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

In another embodiment, the cells described herein may be used for the manufacture of a medicament for the treatment of an immune response in a subject in need thereof. In another embodiment, the invention includes the modified cell described herein for use in a method of treating an immune response in a subject in need thereof.

The cells of the present invention can be administered to an animal, preferably a mammal, even more preferably a human, to treat a cancer. In addition, the cells of the present invention can be used for the treatment of any condition related to a cancer, especially a cell-mediated immune response against a tumor cell(s), where it is desirable to treat or alleviate the disease. Examples of cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like.

In certain embodiments, the subject is provided a secondary treatment. Secondary treatments include but are not limited to chemotherapy, radiation, surgery, and medications.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, allogeniec or xenogenic with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, alymph node, an organ, a tumor, and the like.

The cells described herein can also be administered using any number of matrices. The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized, as such these patents are incorporated herein by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

Sources of T Cells

In certain embodiments, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

Expansion of T Cells

In certain embodiments the T cells can be expanded. Through expansion, T cells can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

Pharmaceutical Compositions

Pharmaceutical compositions of the present invention may comprise the modified cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The cells of the invention to be administered may be autologous, allogeneic or xenogeneic with respect to the subject undergoing therapy.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It can generally be stated that a pharmaceutical composition comprising the modified cells described herein may be administered at a dosage of $10^4$ to $10^9$ cells/kg body weight, in some instances $10^5$ to $10^6$ cells/kg body weight, including all integer values within those ranges. Cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the modified cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

Primary human lymphocytes. Primary human CD4 and CD8 T cells were isolated from healthy volunteer donors after leukapheresis via negative selection, using RosetteSep kits (Stem Cell Technologies. Vancouver BC, Canada). Primary lymphocytes were stimulated with microbeads coated with CD3 and CD28 stimulatory antibodies (Life Technologies, Grand Island, NY, Catalog) as described previously (Barrett et al. (2011) Human Gene Therapy 22(12):1575-1586). T cells were cryopreserved at day 10 in a solution of 90% fetal calf serum and 10% dimethylsulfoxide (DMSO) at $1 \times 10^8$ cells/vial.

Propagation of primary T cells. Primary human T cells were cultured in RPMI 1640 supplemented with 10% FCS, 100-U/ml penicillin, 100-g/ml streptomycin sulfate, 10-mM Hepes, and stimulated with magnetic beads coated with anti-CD3/anti-CD28 at a 1:3 cell to bead ratio. Cells were counted and fed every 2 days and once T cells appeared to rest down, as determined by both decreased growth kinetics and cell size, the T cells were either used for functional assays or cryopreserved.

Design and construction of CRISPRs. CrRNAs were selected by NTTTN20 with NTTT PAM sites. Cpf1 and crRNA targeted constant regions of TCR α, β chains and beta-2 microglobin were transcribed in vitro. CrRNAs were designed to target either a sequence within exon 1 of the TCR α constant region or a consensus sequence common to exon 1 of both TCR β constant regions 1 and 2 and B2m. The mRNA was stored at −80° C. in nuclease-free vials for single use.

Flow cytometry. The following monoclonal antibodies and reagents were used with indicated specificity and the appropriate isotype controls. From BD Biosciences (San Jose, CA): APC-conjugated anti-CD3 (555335), PE-anti-beta-2 microglobin (551337). FITC-anti-HLA (555552). Data were acquired on a FACS Accuri (BD Biosciences, San Jose, CA) using CellQuest version 3.3 (BD Biosciences, San Jose, CA) and analyzed by FCS Express version 3.00 (De Novo Software, Los Angeles, CA) or FlowJo version 7.6.1 (Tree Star, Inc. Ashland, OR).

Gene disruption with CRISPR. T cells were stimulated by CD3/CD28 dynabeads for three days prior to electroporation. Ten million primary T cells were de-beaded prior to electro-transfer of 20 μg Cpf1 (Cas9 or eSpCas9), 10 μg crRNA (or sgRNA) species into the cells with a 360V, 1 ms parameter by BTX830, following a second electro-transfer of 5 μg crRNA (or sgRNA). Or T cells were electroporated with 20 ug Cpf1 mRNA plus 10 ug chemically modified crRNA at the same time. Following electroporation, cells were immediately placed in 2 mL of pre-warmed culture media and cultured at 37° C., 5% $CO_2$, or 32° C., 5% $CO_2$ for 1 day then returned to 37° C., 5% $CO_2$.

```
sgRNA sequence for TRAC:
                            (SEQ ID NO: 1)
AGAGTCTCTCAGCTGGTACA sgRNA sequence for TRBC:
                            (SEQ ID NO: 2)
TGGGAGATCTCTGCTTCTGA
```

```
sgRNA sequence for B2m:
                            (SEQ ID NO: 3)
CGCGAGCACAGCTAAGGCCA crRNA sequence for TRAC:
                            (SEQ ID NO: 4)
GAGTCTCTCAGCTGGTACACGGC crRNA sequence for TRBC:
                            (SEQ ID NO: 5)
AGCCATCAGAAGCAGAGATCTCC crRNA sequence for B2m:
                            (SEQ ID NO: 6)
ATCCATCCGACATTGAAGTTGAC
```

Gene editing with CRISPRs. Cpf1 and Cas9 mRNA was transcribed in vitro with mMESSAGE mMACHINE T7 ULTRA kit (Life Technologies, AM1345, Carlsbad, CA). SgRNA and crRNA were transcribed in vitro using a MEGAscript T7 transcription kit. Chemically modified crRNA was purchased from Integrated DNA Technologies. T cells were stimulated with CD3/CD28 Dynabeads. On day 3, T cells were electroporated with Cas9 or Cpf1 mRNA. Briefly, T cells were washed three times with OPTI-MEM and re-suspended in OPTI-MEM (Invitrogen) at a final concentration of $1-3 \times 10^8$ cells/ml. Subsequently, 0.1 ml of the cell suspension was mixed with IVT RNA and electroporated in a 2 mm cuvette. Twenty micrograms of Cas9 or Cpf1 mRNA and 5 μg of guide RNA were then electroporated into the cells using the BTX830 system (Harvard Apparatus BTX) at 360 V for 1 ms. After electroporation, the cells were immediately placed in 2 ml of pre-warmed culture medium and cultured in the presence of IL-2 (100 IU/ml) at 37° C. under 5% $CO_2$. An additional 5 μg of guide RNA was electroporated into the T cells on day 4.

Measuring allele modification frequencies using the T7E1 assay. The levels of genomic disruption of TRAC, TRBC, and B2m in T cells were determined using a T7E1 Nuclease assay (NEB). The percent target disruption was quantified via densitometry.

The results of the experiments are now described.

Example 1: Enhanced Targeted Mutagenesis Using Stem-Loop crRNA in Primary T Cells Previously, Cpf1 proteins from various genera were tested for genome editing efficiency in mammalian cells (Zetsche et al. Cell. 2015; 163(3):759-771). Among the eight different Cpf1 proteins tested, only two proteins, AsCpf1 and LbCpf1, from the Acidaminococcus (As) and Lachnospiraceae (Lb) genera respectively, were found to produce detectable mutations in mammalian cells. Thus, gene-targeting efficiency of AsCpf1 and LbCpf1 was evaluated herein in T cells. The efficiency of CRISPR-mediated genome editing in primary T cells was compared between AsCpf1, LbCpf1 or Cas9, using a protocol previously developed for efficient T cell gene ablation (Ren et al. (2016) Clinical Cancer Research (2016): clincanres-1300). Cas9 or Cpf1 along with guide RNAs were delivered to primary T cells in a single electroporation. Targeted mutagenesis was measured at three endogenous target sites, the TCR α chain constant region (TRAC), the TCR β constant region (TRBC) and β-2 microglobulin (B2m). 10% to 20% targeted mutagenesis was observed using Cas9, whereas no detectable mutagenesis was observed with either AsCpf1 or LbCpf1. With multiple deliveries of guide RNAs, 80-90% gene disruption was achieved at all three gene loci using Cas9.

Figure 4:
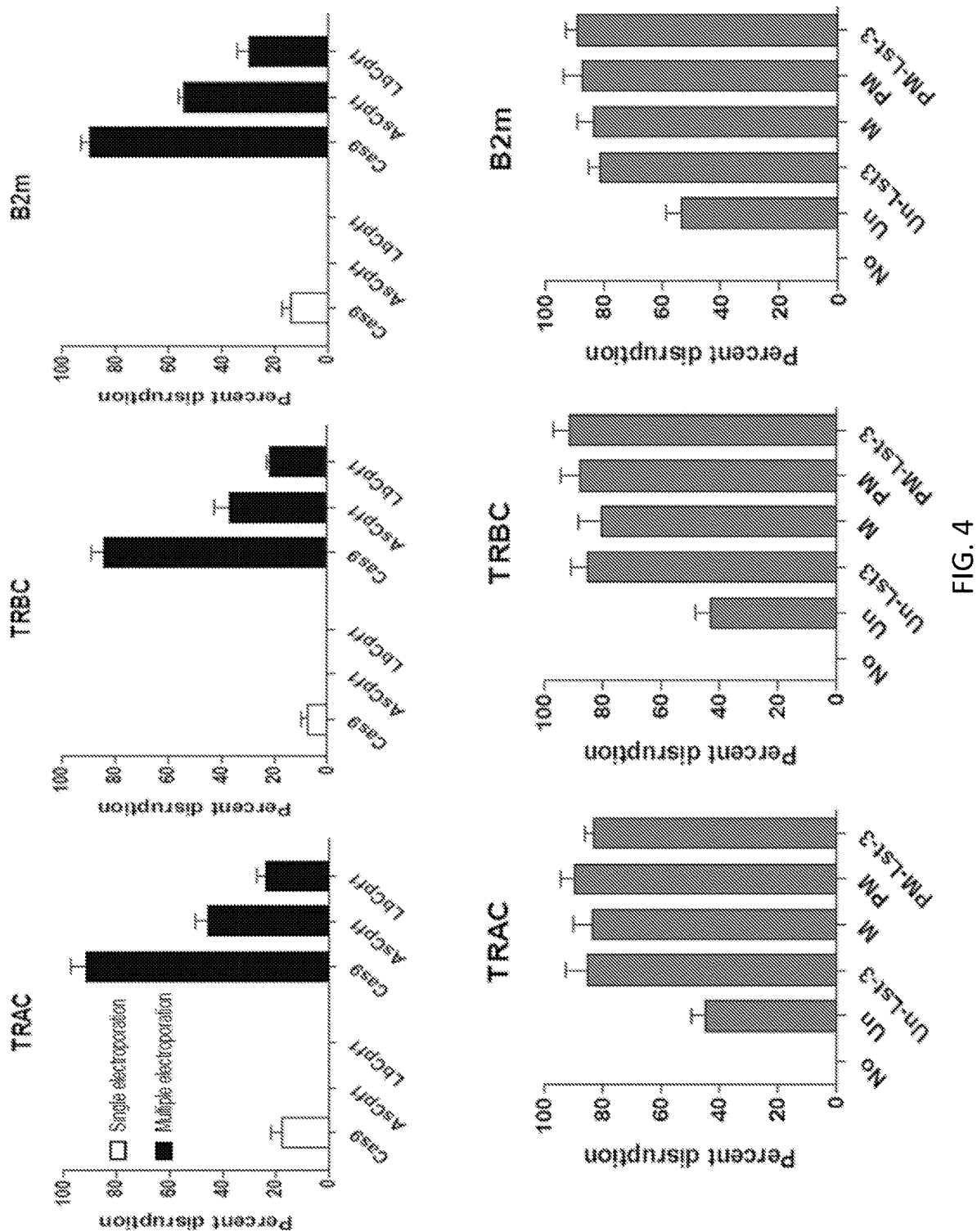
FIG. 4 is a series of plots illustrating enhanced gene disruption with stem-loop crRNA in primary T cells.

Over 50% gene disruption was achieved using AsCpf1 and approximately 30% was achieved using LbCpf1 (FIG. 4). The improved efficacy of gene disruption was associated with a delayed second delivery of guide RNA after Cas9 and Cpf1 electroporation. This finding indicated that small guide RNAs, including sgRNA and crRNA, are much more prone to degradation than Cas9 and Cpf1 mRNAs. Because AsCpf1 exhibited a substantially higher gene-disruption efficiency than LbCpf1, AsCpf1 was focused on in subsequent experiments.

Figure 1B:
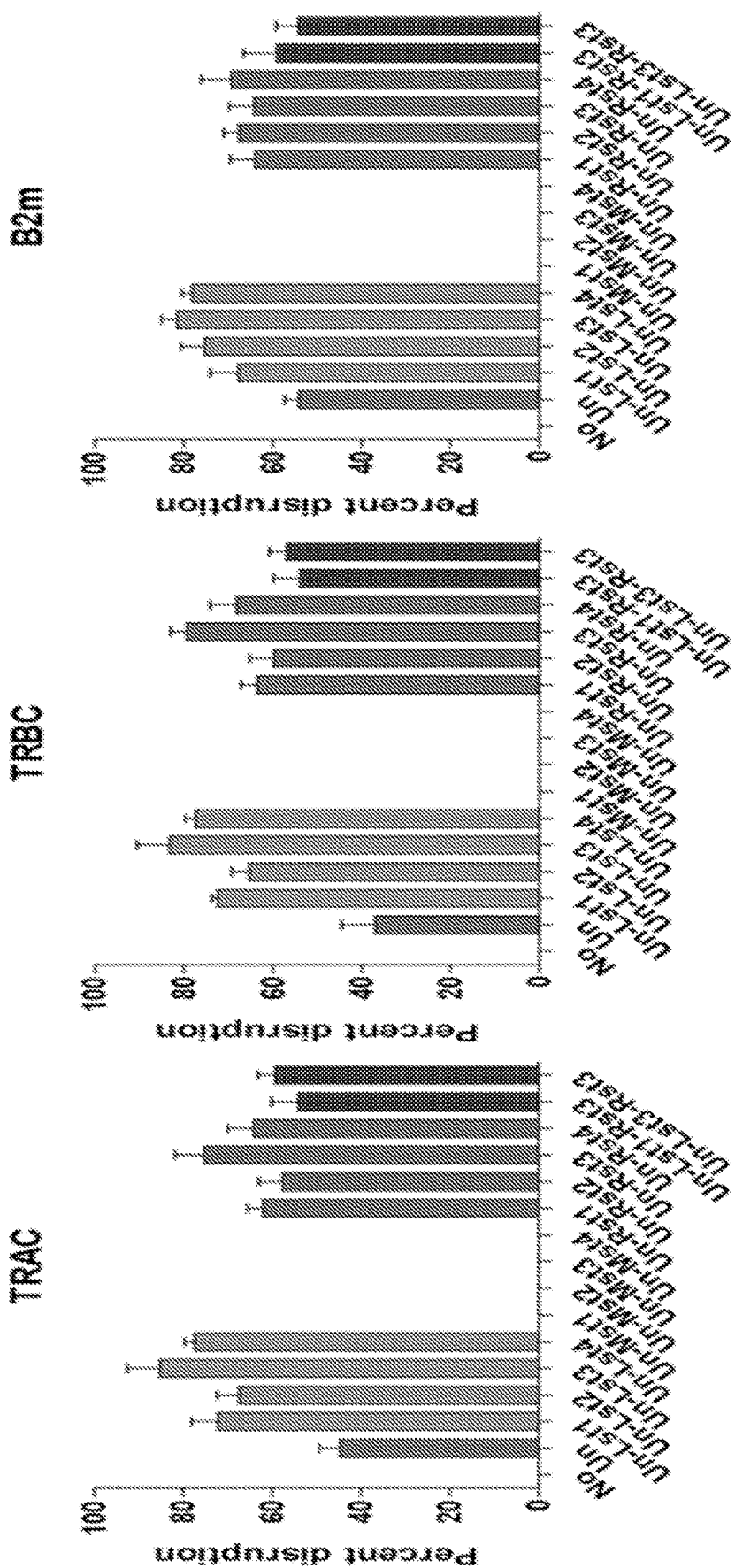

Although gene targeting with Cpf1-crRNA achieved substantial gene ablation in T cells, the efficiency was lower than for Cas9-sgRNA. The structural difference between the sgRNA and crRNA might account for the difference in stability. Interestingly, it was found that sgRNA differs from crRNA in terms of various stem-loop structures that interact with Cas9, thus protecting sgRNA from RNases. Stem loops have been reported to enhance the stability of RNAs by decreasing the activity of RNases. An A-U flip and extension of the stem loop has been shown to increase the stability of sgRNA. And, the efficiency of gene disruption has been shown to be enhanced by optimizing the structure of sgRNA. Herein, it was tested whether the gene-disruption efficiency could be increased by adding stem loops to crRNA to generate stem-loop crRNA (st-crRNA) (FIG. 1A). An increase of approximately 2-fold was observed for all three targeted genes after the introduction of different stem-loop structures of sgRNA at either the 5' (Lst) or 3' (Rst) terminus of crRNA. The 5'-terminal stem-loop structure-3 (Lst-3) resulted in the greatest increase in gene disruption, which reached 85% (83.6%±7.3, n=5) for TRAC, 83% (81.7±5.7, n=4) for TRBC and 81% (78.7±8.4, n=4) for B2m (FIG. 1B). However, elongation of the original handle stem-loop in crRNA (Mst-crRNA) abolished its function, and adding stem loops at both the 5' and 3' termini decreased the targeting efficiency, thus elucidating the structural requirements and length limitations of crRNA for Cpf1 binding (FIG. 1B).

Figure 1C:
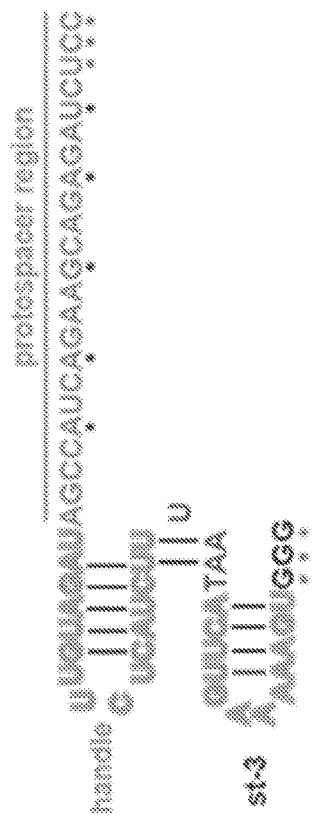
Figure 1E:
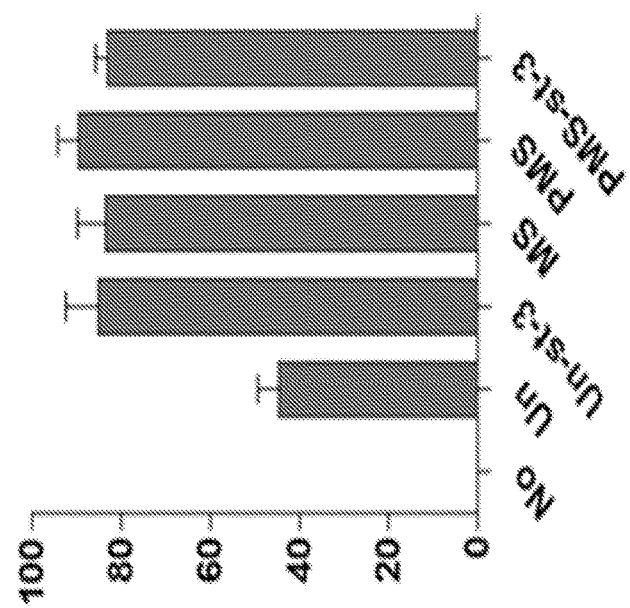
Figure 1D:
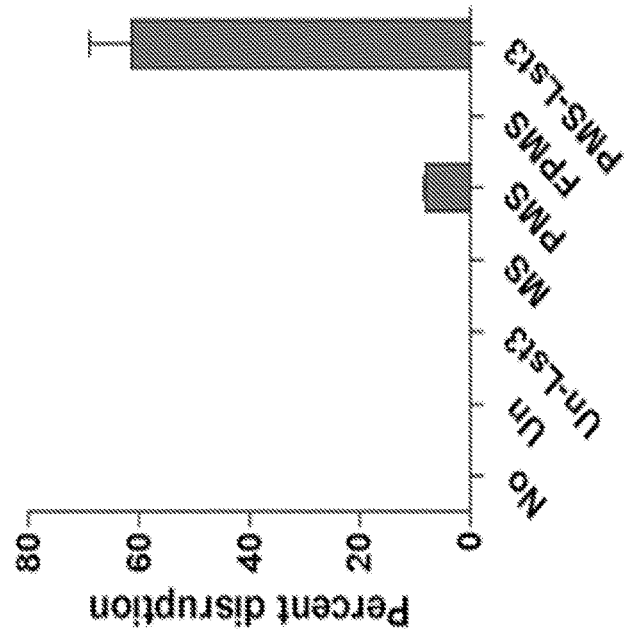
Figure 5:
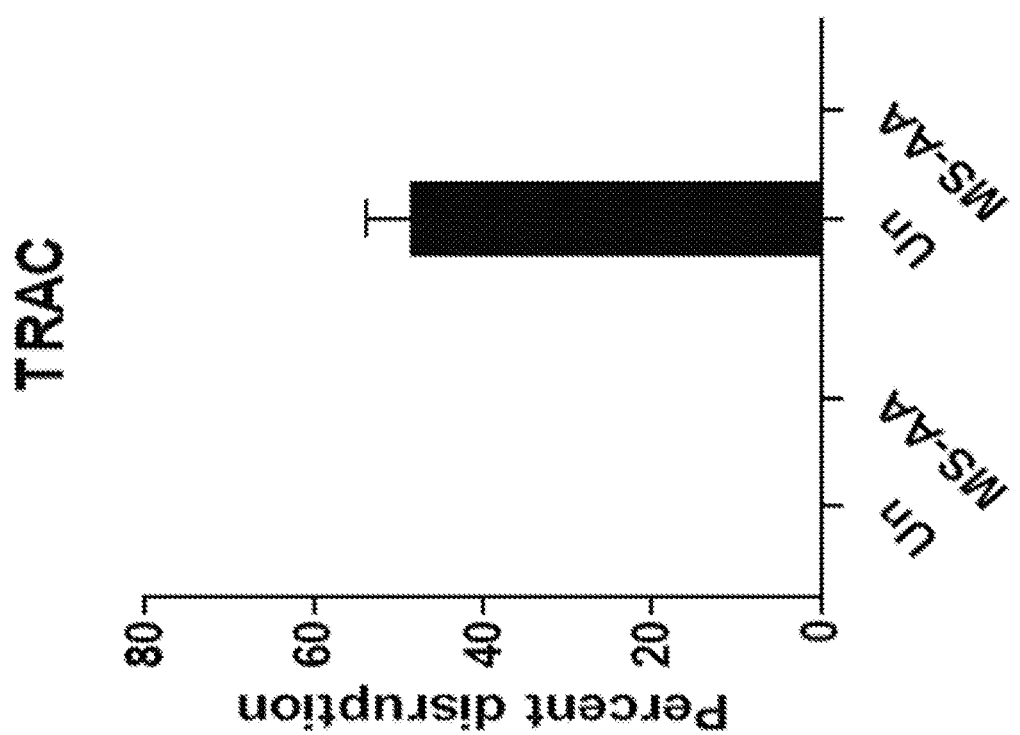
FIG. 5 is a plot illustrating chemical modification on the handle structure of crRNA abolishes its function. TRAC disruption using handle "AA" chemically modified crRNA with single and multiple electroporation protocols are displayed.

Example 2: Enhanced Targeted Mutagenesis with Chemically Modified Stem-Loop crRNA Chemical modification to increase the stability of sgRNAs has been shown to enhance gene-disruption efficiency. To further increase the stability of crRNA, chemically modified crRNAs targeting TRAC were generated herein. It was also determined whether efficient gene disruption could be achieved with a single electroporation, thus decreasing the toxicity caused by a second electroporation. To confirm that the chemical modification did not abolish the crRNA's function, the modified crRNAs were tested with two electroporation protocols. Modification of the tail "AA" nucleotides in the crRNA handle abolished its function, thus indicating that "AA" is indispensable for proper handle structure formation (FIG. 5). To avoid this effect, three "G" residues were added to the handle tail and then 2'-O-methyl 3'phosphorothioation (MS) was performed on the three "Gs" and three tail protospacer nucleotides (FIG. 1C). In this case, modification did not abolish the crRNA's function, although gene disruption was still not observed after a single electroporation of Cpf1 and MS-crRNA. Using a partially phosphorothioated protospacer MS-crRNA (PMS-crRNA), 9.1% (9.7±1.7, n=3) gene disruption of TRAC was achieved. However, full phosphorothioation of the crRNA (FPMS-crRNA) abolished its function, thus indicating that the crRNA is vulnerable to modification of its handle structure (FIG. 1D).

To validate the function of the stem-loop structures on crRNAs, PMS-Lst-3 crRNA targeting TRAC was generated. After a single electroporation of Cpf1 and non-modified Lst-3-crRNA, no gene disruption was observed; however, PMS modification of Lst-3 crRNA resulted in over 61% (58.3±6.5, n=3) TRAC disruption, which was nearly 7 times the disruption obtained with PMS-crRNA without a stem loop (FIG. 1D).

Although the presence of PMS modification together with a stem-loop greatly enhanced the Cpf1-crRNA gene-targeting efficiency in a single electroporation protocol, it did not further improve the gene-disruption efficiency of stem-loop crRNA in the two-electroporation protocol. This suggests that the stem-loop structure provides sufficient protection of crRNA in experiments in which only transient crRNA exposure is required (FIG. 1E).

Example 3: Stringent Guide Selectivity of Cpf1 in Primary T Cells

Figure 2A:
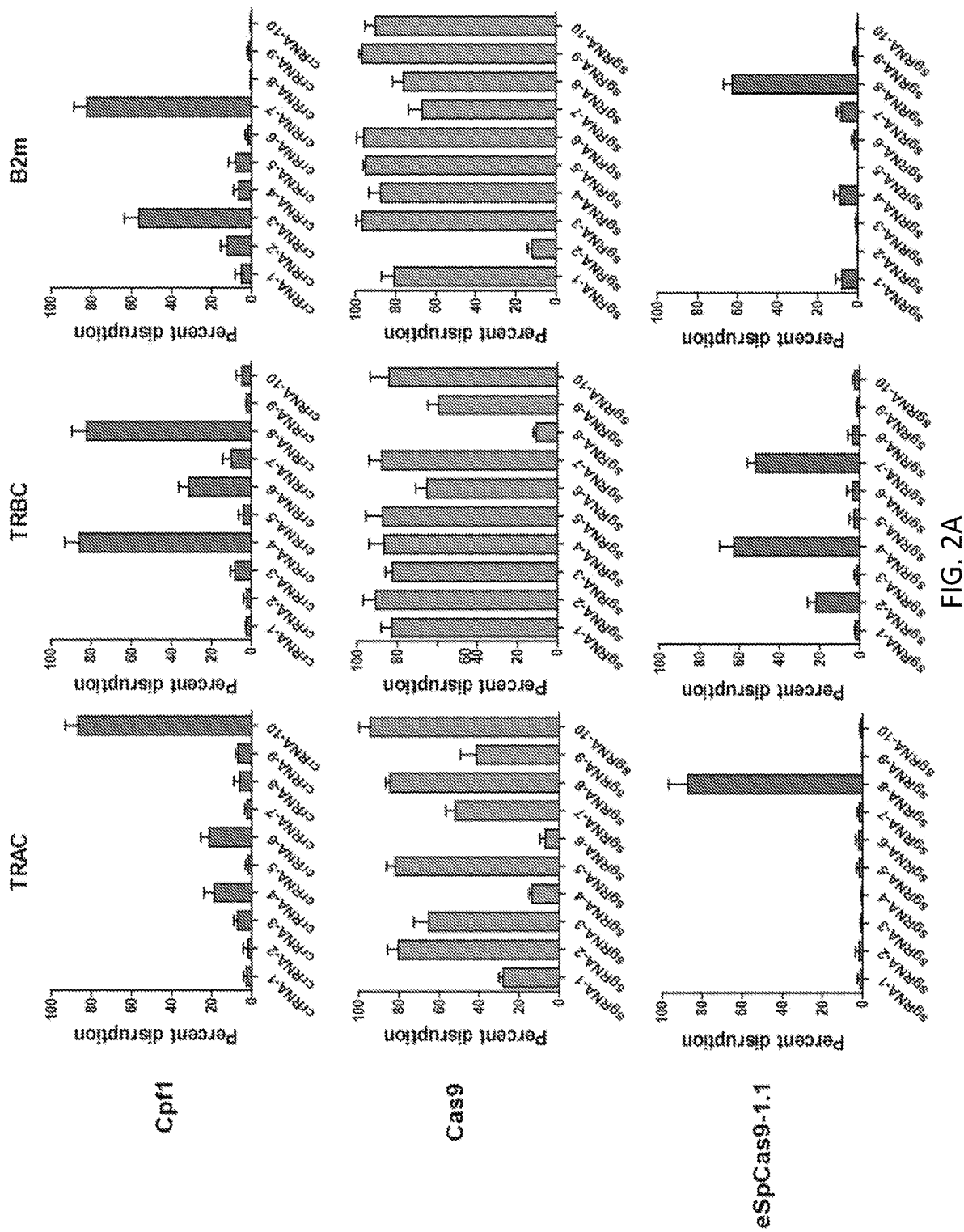
FIGS. 2A-2B are a series of plots illustrating stringent guide selectivity of Cpf1 in primary T cells.
Figure 2B:
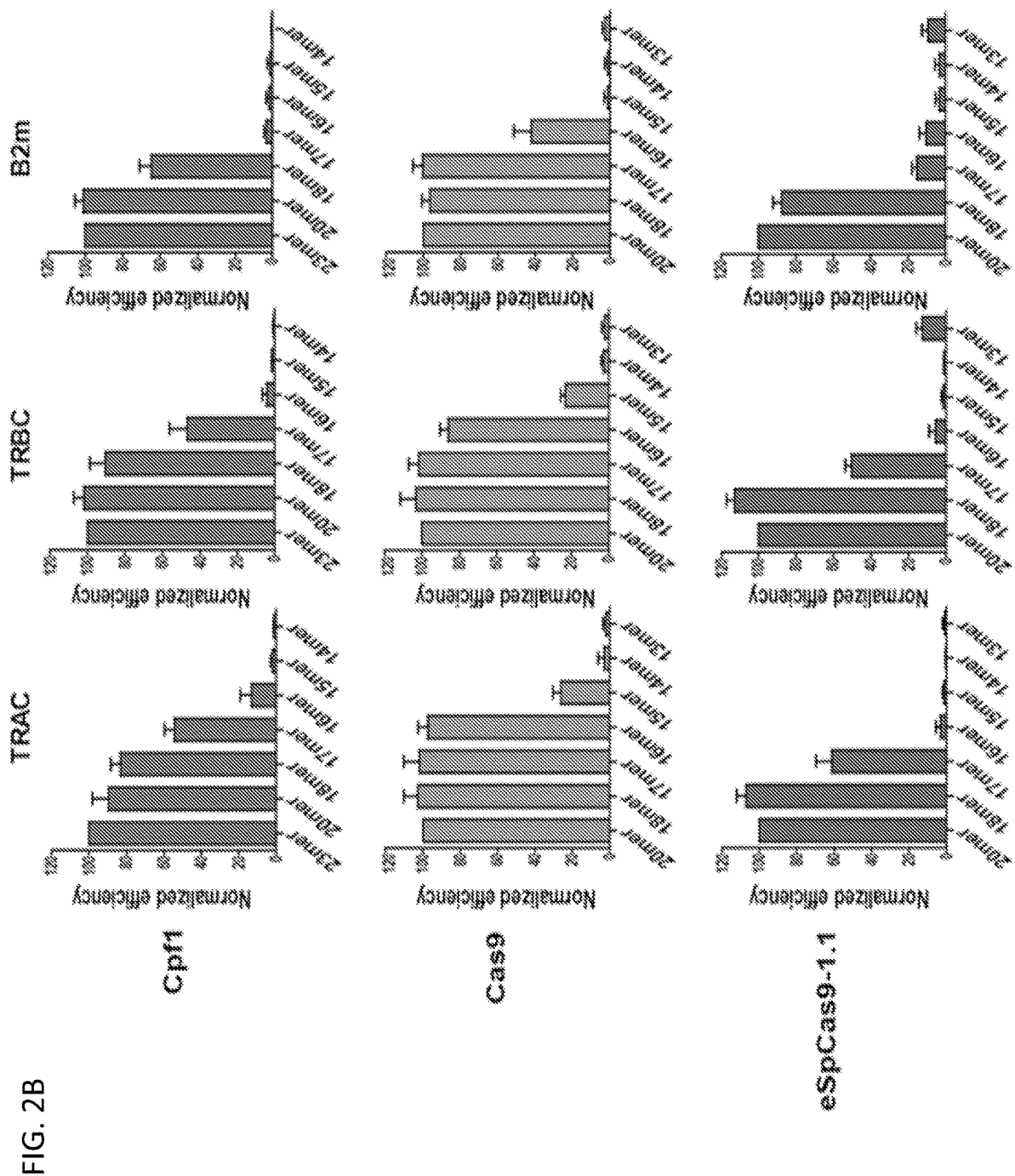

To test the features of Cpf1 in T cells, gene disruption was performed with Cpf1 and st-crRNAs in primary T cells. Cpf1 differs from Cas9 not only in the use of crRNA instead of sgRNA, but it also recognizes a more stringent PAM sequence of TTTN, whereas Cas9 recognizes a PAM sequence of NGG. Cpf1 disrupts target genes in an equally efficient, but more stringent manner than Cas9. Ten different crRNAs or sgRNAs targeting TRAC, TRBC and B2m gene loci were used to test the performance of Cpf1, Cas9 and eSpCas9-a high-fidelity Cas9 in T cells. More than half the sgRNAs mediated efficient gene disruption with Cas9, whereas Cpf1 achieve equivalent gene disruption with only 1 to 2 of the 10 crRNAs. These results indicated that the selection of crRNA by Cpf1 is more stringent than the selection by Cas9. Interestingly, this feature of Cpf1 is similar to that of eSpCas9, a high-fidelity Cas9 that also showed equivalent gene disruption, but more stringent sgRNA selection (FIG. 2A). Enhanced specificity has been reported through use of shorter truncated sgRNAs. Hence, it was tested whether a similar strategy could be used by Cpf1-crRNA to increase gene-targeting specificity. In contrast to Cas9, which can use an sgRNA as short as 16 bp with only a slightly decreased gene-disruption efficiency, crRNA truncated to even 17 bp resulted in completely abolished function of Cpf1, a result similar to that observed for eSpCas9 (FIG. 2B). Thus, Cpf1 behaves similarly to eSp-Cas9 in terms of both guide selectivity and truncated RNA, demonstrating that Cpf1 can be used as an alternative to Cas9 as a high-fidelity gene-editing tool.

Figure 3A:
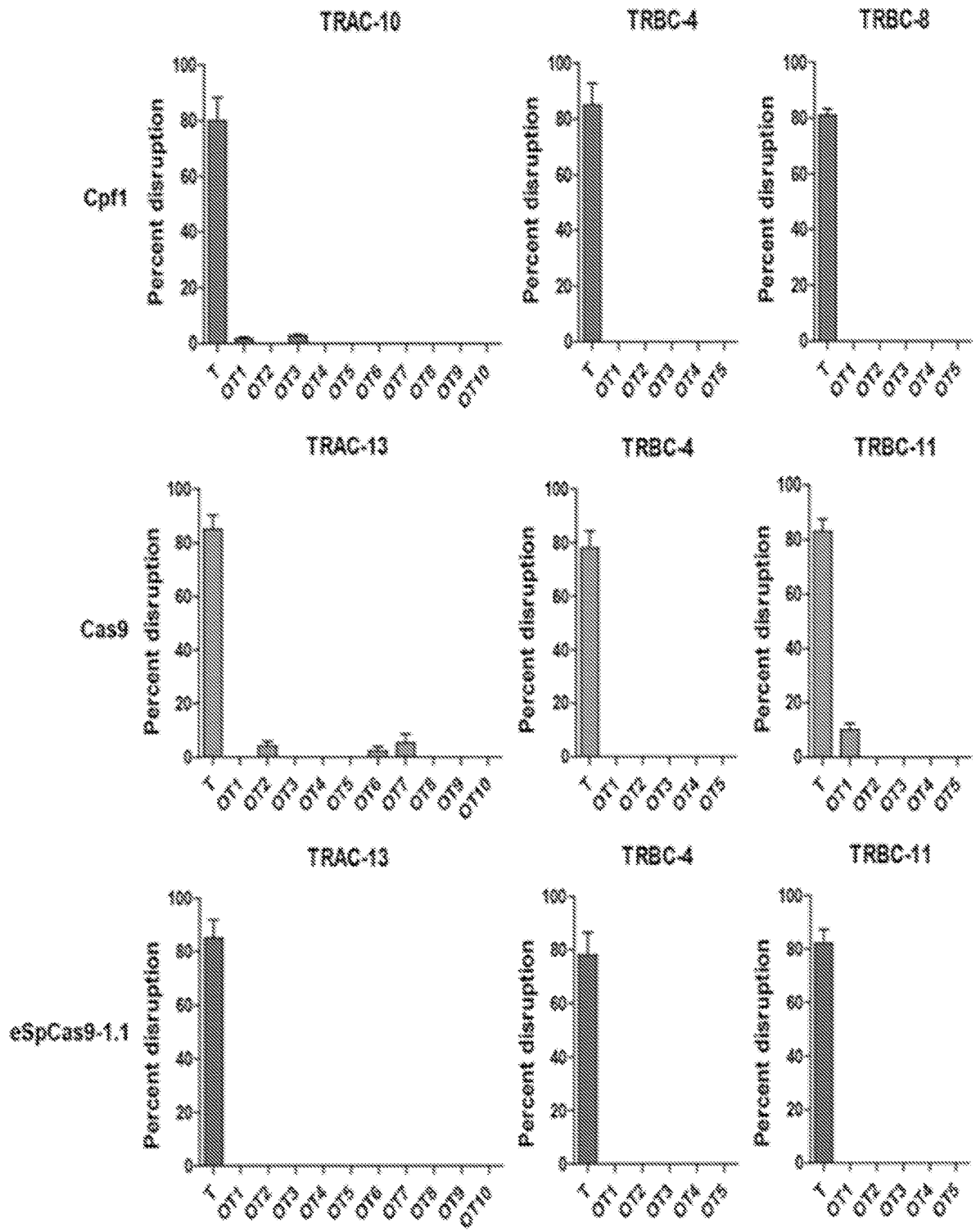
FIGS. 3A-3C are a series of plots illustrating enhanced gene-targeting specificity with Cpf1 in primary T cells. TRAC, TRBC, B2m gene ablation was performed to measure off-target events of different RGENs. The frequency of mutagenesis was measured via the T7E1 assay. Gene targeting was conducted with either a 20 mer guide RNA (FIG. 3A) or an 18 mer guide RNA (FIG. 3B), and off-target effects of different RGENs were tested using mutated guide RNAs. Frequencies of mutagenesis at target and off-target sites were calculated via the T7E1 assay.

Example 4: Enhanced Gene-Targeting Specificity of Cpf1 Compared to Cas9 in Primary T Cells To further test the safety of Cpf1, off-target events were measured using the 3 crRNAs with the highest gene-disruption efficiency in targeting TRAC, TRBC and B2m. Ten off-target sites were measured for each gene. In agreement with the stringent guide selectivity, much lower levels of and fewer off-target events were observed for Cpf1 and eSpCas9 compared with Cas9, using either a wild-type 20 bp or truncated 18 bp guide RNA (FIG. 3A).

To test how faithful Cpf1 and Cas9 were to their guide RNAs, each nucleotide of the sgRNA or crRNA targeting TRAC and TRBC was mutated. A single point mutation adjacent to the PAM site of Cas9 sgRNA had a severe effect on its function, whereas little or no effect was observed if the mutation site was 10 base pairs away from the PAM site.

Figure 3B:
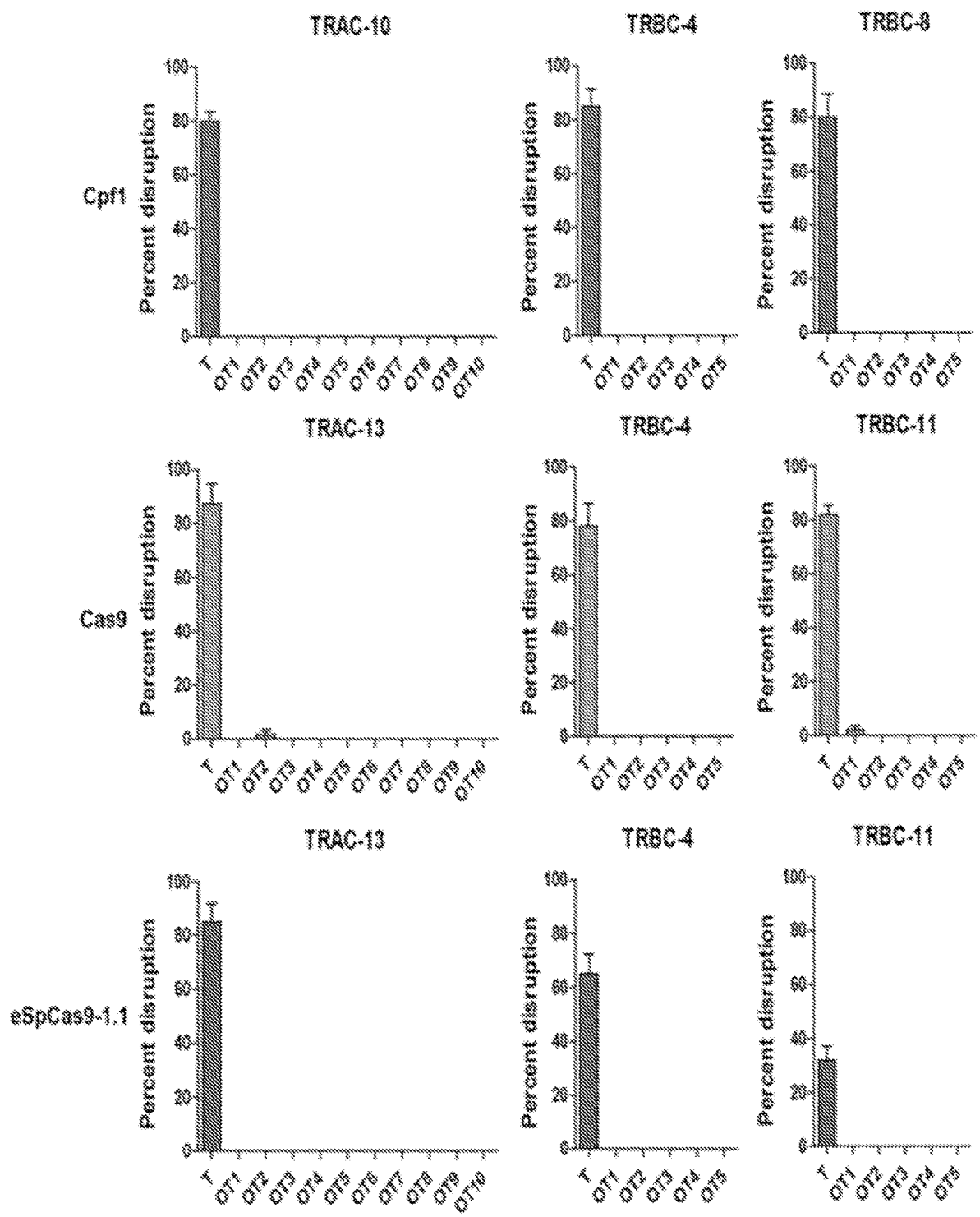
Figure 3C:
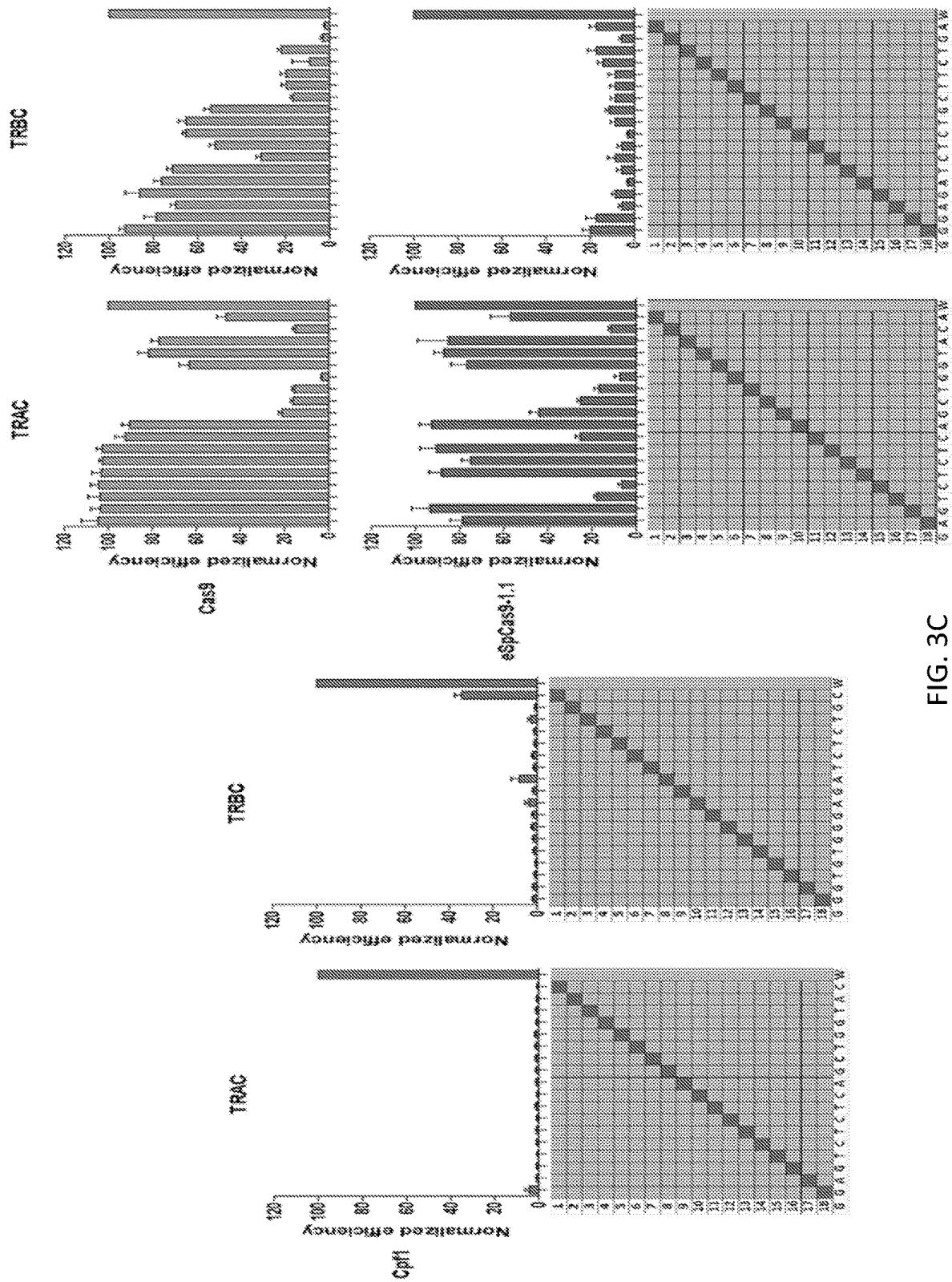

However, even a single mutation in the crRNA was able to completely abolish the function of Cpf1, regardless of where the mutation site was located. Interestingly, mutation of sgRNA targeting TRBC abolished the function of eSpCas9, whereas mutation of sgRNA targeting TRAC resulted in retention of most of the function of eSpCas9 (FIG. 3B). This finding indicated that Cpf1 might be even more faithful to its guide RNA than eSpCas9.

All of these data indicate different target DNA recognition machineries of Cpf1 and Cas9. Additionally, in contrast to NGG, which is mainly distributed among coding sequences in exons, many TTTN sequences are located within untranslated regions, thus leading to less severe off-target-associated functional effects of Cpf1 than Cas9.

Example 5: Discussion

As one of the most attractive applications of the CRISPR system, highly efficient gene editing holds great promise for advancing T cell-based adoptive immunotherapy. However, little is known about the features of the Cas9 homolog Cpf1 and its guide crRNA. Until now, the potential for targeted genome editing in T cells using Cpf1 had yet to be explored. The present study demonstrated that efficient and specific gene disruption can be achieved using Cpf1-crRNA.

Over 40-50% gene ablation can be accomplished via multiple delivery of crRNA, but this high efficiency also results in toxicity to T cells. To minimize the toxicity associated with multiple electroporations, structural and chemical modifications of crRNAs were performed. Over 80% gene disruption was achieved through use of multiple deliveries of stem-loop-crRNAs. However, no substantial gene disruption was observed after a single electroporation. Enhanced gene disruption has been reported through use of 2'-O-methyl 3'phosphorothioated (MS) chemically modified sgRNA, but MS modification of crRNA herein did not result in detectable gene disruption after a single electroporation. Although gene editing with partial phosphorothioation of crRNA resulted in only 9% gene disruption, by incorporating protective stem loops into the crRNA, an increase in gene targeting of nearly 7-fold was achieved, reaching over 60%.

CrRNA was found to be very sensitive to modifications of its handle structure, since modification of either the tail AA or the inner nucleotides abolished its function. This finding suggested that the structure of crRNA is critical to its formation, and thus, modifying the handle structure might disrupt its interaction with Cpf1. Elongation of the handle stem-loop of crRNA also abolished its function, thus indicating the space limitation of the Cpf1 binding pocket, which was previously elucidated in the crystal structure of Cpf1 in complex with a crRNA.

Gene editing with Cpf1, compared with Cas9, resulted in less off-target mutagenesis for all three tested endogenous genes. Fidelity to guide RNAs, as assessed on the basis of tolerance to mutations in crRNA and sgRNA, also demonstrated that Cpf1 is more precise than Cas9 in T cells. Although both Cas9 and Cpf1 generate DSBs, Cas9 uses its RuvC- and HNH-like domains to produce blunt-ended cuts within the seed sequence, whereas Cpf1 uses a RuvC-like domain to produce staggered cuts outside the seed sequence. As indicated by the crystal structure, targeted cleavage requires the dissociation of double-stranded target DNA, caused by interaction of Cas9 with the PAM sequence. This result might indicate that less energy is required for Cas9 to dissociate double-stranded DNA through cleavage within the seed region than for Cpf1 to cut sites outside the seed region. This property might in turn result in the higher off-target potential of Cas9 than Cpf1.

In summary, it was demonstrated herein that the CRISPR/Cpf1 system is an efficient and high-fidelity gene-editing tool in T cells.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of gene editing comprising administering to a cell:
   (a) an exogenous nucleic acid comprising a stem-loop Clustered Regularly Interspaced Short Palindromic Repeats (CRISPR) RNA (st-crRNA) comprising:
      (i) a crRNA comprising a target binding sequence that hybridizes to a target nucleic acid sequence in the cell,
      (ii) a handle stem-loop structure attached to the 5'-end or the 3'-end of the target binding sequence, and
      (iii) an additional stem-loop structure attached to the 5' or 3' end of the handle stem-loop structure,
      wherein the st-crRNA molecule does not comprise stem-loop structures on both the 5' and 3' end of the crRNA, and
      wherein the handle stem-loop structure is not modified with 2'-O-methyl 3'phosphorothioation (MS); and
   (b) an exogenous nucleic acid encoding a Cpf1 enzyme, wherein the st-crRNA and the Cpf1 enzyme form a RNA-guided DNA endonuclease (RGEN) complex to edit the target nucleic acid sequence.

2. The method of claim 1, wherein the cell is a T cell.

3. The method of claim 2, wherein the T cell is a primary T cell.

4. The method of claim 1, wherein the administering comprises electroporating the exogenous nucleic acids into the cell.

5. The method of claim 4, wherein the electroporating is performed multiple times.

6. The method of claim 1, wherein the Cpf1 enzyme comprises Acidaminococcus Cpf1 (AsCpf1).

7. The method of claim 1, wherein the Cpf1 enzyme comprises Lachnospiraceae Cpf1 (LbCpf1).

8. The method of claim 1, wherein the st-crRNA comprises a stem-loop structure on the 3' end of the crRNA.

9. The method of claim 1, wherein the st-crRNA comprises a stem-loop structure on the 5' end of the crRNA.

10. The method of claim 9, wherein the stem-loop structure further comprises three guanine (G) residues added to the 5' end of the additional stem-loop structure, and wherein the three G residues added to the 5' end of the additional stem loop structure are modified with 2'-O-methyl 3'phosphorothioation (MS).

11. The method of claim 10, wherein the protospacer region of the st-crRNA further comprises a partial phosphorothioation (PMS) modification.

12. The method of claim 1, wherein the gene editing comprises mutating a gene selected from the group consisting of: TCR α chain constant region (TRAC), TCR β constant region (TRBC), and β-2 microglobulin (B2m).

* * * * *